United States Patent
Hobson et al.

(10) Patent No.: US 6,410,603 B1
(45) Date of Patent: Jun. 25, 2002

(54) ACTIVE TOPICAL SKIN PROTECTANTS USING COMBINATIONS OF REACTIVE NANOPARTICLES AND POLYOXOMETALATES OR METAL SALTS

(75) Inventors: Stephen T. Hobson, Belcamp; Ernest H. Braue, Witeford; Erich K. Lehnert, Rosemont, all of MD (US); Kenneth J. Klabunde; Shawn Decker, both of Manhattan, KS (US); Craig L. Hill, Atlanta, GA (US); Jeffrey Rhule, Franklin, OH (US); Eric Boring, Diamondhead, MS (US); Olga Koper, Manhattan, KS (US)

(73) Assignees: The United States of America as represented by the Secretary of the Army, Washington, DC (US); Nanoscale Materials, Inc.; Emory University, both of Atlanta, GA (US)

( * ) Notice: Subject to any disclaimer, the term of this patent is extended or adjusted under 35 U.S.C. 154(b) by 0 days.

(21) Appl. No.: 09/871,744

(22) Filed: Jun. 1, 2001

Related U.S. Application Data
(60) Provisional application No. 60/209,337, filed on Jun. 2, 2000.

(51) Int. Cl.⁷ .................. A61K 31/02; A61K 31/08; A61K 47/00; A61K 7/42
(52) U.S. Cl. .................. 514/759; 424/59; 514/723; 514/772; 514/789; 514/844; 514/845; 514/937; 514/944
(58) Field of Search .................... 424/59; 514/723, 514/759, 772, 789, 844, 845, 937, 939, 944

(56) References Cited

U.S. PATENT DOCUMENTS

| | | | |
|---|---|---|---|
| 4,649,037 A | 3/1987 | Marsh et al. | 423/338 |
| 5,607,979 A | 3/1997 | McCreery | 514/759 |
| 5,914,436 A | 6/1999 | Klabunde et al. | 588/205 |
| 5,990,373 A | 11/1999 | Klabunde | 588/200 |
| 6,057,488 A | 5/2000 | Koper et al. | 588/200 |
| 6,224,885 B1 | 5/2001 | Jenner | 424/401 |

OTHER PUBLICATIONS

Smith, et al., Jrnl. of the American Acad. of Dermatology, Vo. 32, No. 5, part 1, May 1995, pp. 765–776, Sulfur mustard: Its continuing threat as a chemical warfare agent, the cutaneous lesions induced, progress in understanding its mechanism of action, its long–term health effectgs, and new developments for protection and therapy.

Arroyo, er al., Jrnl. of Pharm. and Toxicol. Methods, vol. 33, No. 2, Apr. 1995, pp. 109–112, EPR/Spin–Label Technique as an Analytical Tool for Determining the Resistance of Reactive Topical Skin Protectants (rTSPs) to the Breakthrough of Vesicant Agents.

*Primary Examiner*—Shelley A. Dodson
(74) *Attorney, Agent, or Firm*—Elizabeth Arwine

(57) ABSTRACT

A topical skin protectant formulation containing a barrier cream and a active moiety for protecting warfighters and civilians against all types of harmful chemicals, specifically chemical warfare agents (CWAs). The topical skin protectant offers a barrier property and an active moiety that serves to neutralize chemical warfare agents into less toxic agents.

25 Claims, 1 Drawing Sheet

ACTIVE TOPICAL SKIN PROTECTANTS USING COMBINATIONS OF REACTIVE NANOPARTICLES AND POLYOXOMETALATES OR METAL SALTS

PRIORITY INFORMATION

This application claims the benefit of priority of U.S. Provisional Application No. 60/209,337 filed Jun. 2, 2000.

BACKGROUND OF THE INVENTION

1. Field of the Invention

This invention relates to active topical skin protectants. More specifically, the invention relates to an active barrier cream for protection against all types of harmful chemicals, specifically chemical warfare agents (CWAs). The active barrier cream is applied prior to exposure on the skin of persons at risk of exposure to harmful chemicals to provide a protective barrier for the skin. The active barrier cream chemically or physically reacts with harmful chemicals such as CWAs (vesicants and nerve agents) to neutralize these harmful chemicals while the barrier properties of the cream prevent penetration of harmful chemicals through the cream to the skin.

2. Description of Related Art

The concept of applying a topical protectant to vulnerable skin surfaces before entry into a chemical combat arena has been proposed as a protective measure against percutaneous CWA toxicity since the first use of CWAs in World War I. The protectant was applied to vulnerable skin surfaces prior to entry into a chemical combat area. Topical protectants should augment the protection afforded by the protective overgarments and/or redefine the circumstances requiring mission oriented protective posture (MOPP) levels. The rapid action of vesicating agents, also known as blistering agents, such as sulfur mustard (HD) and lewisite (L), require a pre-exposure skin protection system or a contamination avoidance approach that may preclude the percutaneous toxicity of these agents. These approaches also reduce the risk of exposure to organophosphorus (OP) chemical agents (nerve agents), which unlike the vesicating agents, are lethal in droplet amounts.

An organic molecule, S-330, that reacts with CWAs was incorporated in a product and fielded as the M-5 ointment kit at the end of World War II (Formula 1).

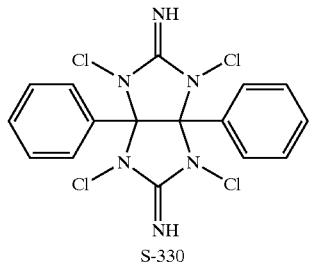

Formula 1

S-330

However, the unacceptable barrier properties and the undesirable cosmetic properties (specifically foul odor and sticky texture) caused a recall of this product.

Two non-active topical skin protectant (TSP) formulations were developed at the United States Army Medical Research Institute of Chemical Defense (USAMRICD) and were transferred to advanced development following a Milestone Zero (MS0) Review in October 1990. The timeline of the approval of the TSP continued with MSI in 1993, a Investigational New Drug (IND) filed with the FDA in 1994, MSII in 1995, and culminated with New Drug Application (NDA) approval in February, 2000. Upon approval by the FDA, the TSP was designated Skin Exposure Reduction Paste Against Chemical Warfare Agents (SERPACWA). SERPACWA is a 50:50 (wt/wt) mixture of perfluoropolyether oil (Fomblin® Y25 from Ausimont) and poly (tetrafluoroethylene) (polymist® F5a powder from Ausimont). The formulation described in McCreery U.S. Pat. No. 5,607,979 is directed to a topical skin protectant cream that acts as a barrier to CWAs.

Although SERPACWA extends the protection afforded by MOPP and allows a longer window for decontamination, it does not completely remove the possibility for contamination because the CWA is not neutralized. To avoid contamination of other areas of the battlefield and to preclude the future percutaneous absorption of the CWA, decontamination is still required. Furthermore, although the McCreery formulation provides excellent protection against GD and HD liquid, its protection against HD vapor is minimal.

To overcome these deficiencies, there is a need for a new TSP that contains an active component. This active Topical Skin Protectant (active TSP) was developed within the following criteria. First, the active TSP should neutralize CWAs including but not limited to sulfur mustard (HD), soman (GD), and VX. Second, the barrier properties of the TSP should be maintained or increased. Third, the protection against HD vapor should increase. And fourth, the cosmetic characteristics (i. e. odor, texture) of the TSP should be maintained.

This invention meets the above criteria and solves the problems associated with the past TSPs by providing an active topical skin protectant that increases effectiveness of the TSP barrier quality and neutralizes CWAs into less harmful products.

It is therefore, an objective of the present invention to provide an active topical skin protectant that prevents the percutaneous absorption of CWAs and converts these toxic materials into less harmful products.

It is a further objective of the present invention to provide an active topical skin protectant that maintains desirable cosmetic properties making it acceptable to the user. Specifically, the active TSP should not be sticky, should be without offensive odor, and should be nonirritating to the skin.

It is still a further object of the invention to provide an active topical skin protectant that is practical for field operations. Specifically, the active TSP should have a stable shelf life, not be easily washed off with water, and should not react with insecticides or camouflage paint.

SUMMARY OF THE INVENTION

A topical skin protectant formulation for neutralizing chemical warfare agents into less toxic products comprising: a barrier base cream and one or more active moieties. The base cream comprises poly(tetrafluoroethylene) resins dispersed in perfluorinated polyether oils. The active moieties that have been found to be effective with the base cream are listed in Table 1. The active barrier cream is applied to the skin prior to exposure of persons at risk of exposure to harmful chemicals to provide an active barrier to protect the skin. The active barrier cream chemically or physically reacts with harmful chemicals such as CWAs to neutralize these harmful chemicals while the barrier properties of the cream prevent penetration of harmful chemicals through the cream to the skin.

DETAILED DESCRIPTION

Candidate Active Moieties

Figure 1:
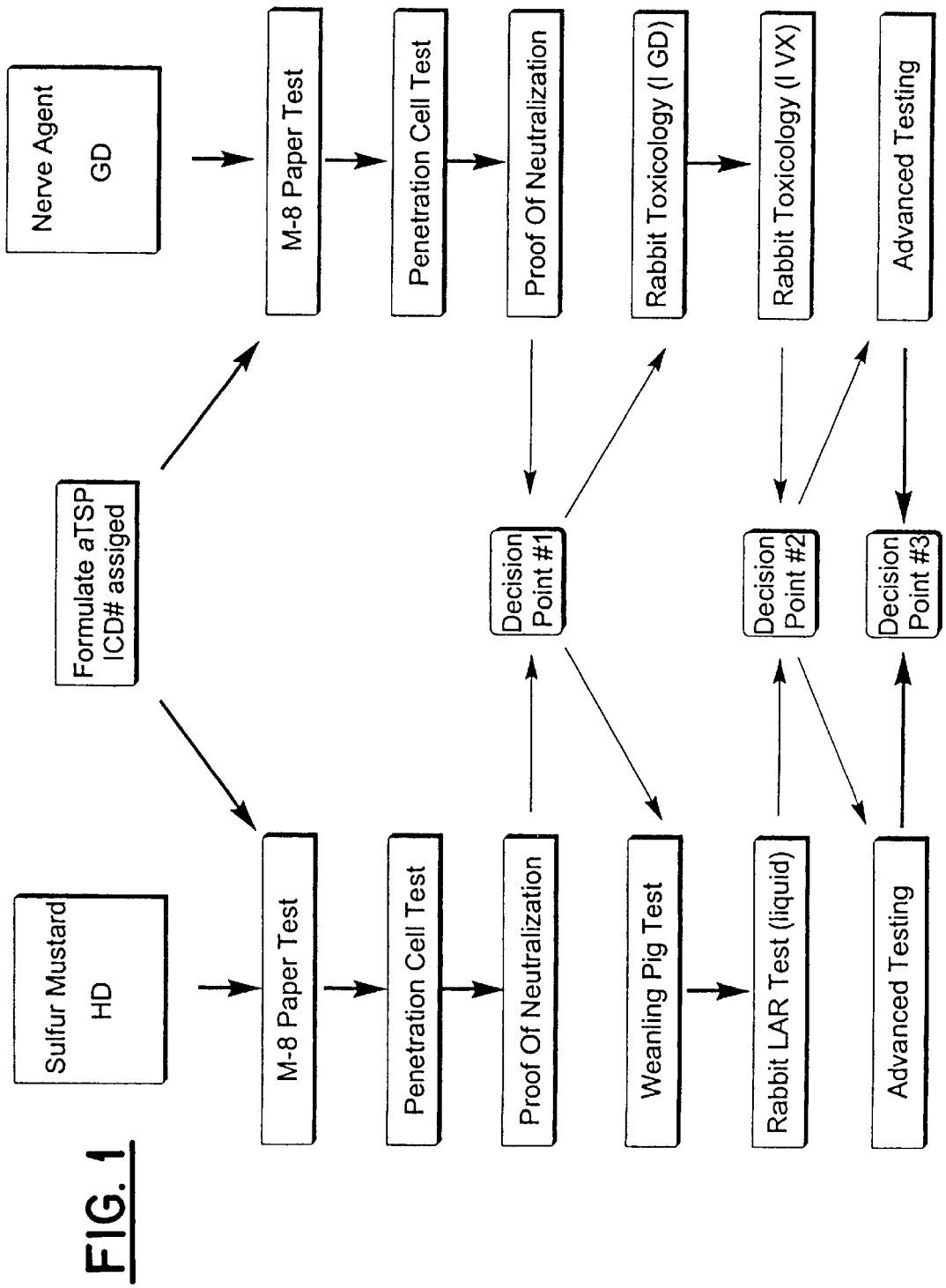
FIG. 1 is a flow diagram of the active TSP Decision Tree Network for efficacy evaluation.

The types of materials that neutralize harmful agents use three main modes of action: oxidation, reduction or hydrolysis.

Operating criteria, however, restricts the selection of the active materials. Thus, the active moiety must not irritate the skin, react with insecticides or camouflage paints or be unstable. This restriction eliminates many of the most active species. Furthermore, the active moiety must be incorporated into a highly fluorinated environment that is not amenable to many reaction pathways. One class of compound that is amenable to these conditions is composite materials composed of reactive nanoparticles (RNPs) and polyoxometalates (POMs) or metal salts.

TABLE 1

LIST OF EXAMPLE ACTIVE COMPOUNDS AND EXAMPLE FORUMLATIONS FOR ACTIVE TOPICAL SKIN PROTECTANTS USING COMBINATIONS OF REACTIVE NANOPARTICLES AND POLYOXOMETALATES OR METAL SALTS

| | | Example Formulation | | |
|---|---|---|---|---|
| ICD # | Active POM/Nanoparticle | % Active | % PFPE | % PTFE |
| 3353 | $[Na_5PV_2Mo_{10}O_{40}]$Aerogel-$TiO_2$ | 5 | 47.5 | 47.5 |
| 3520 | $[Ag_5PV_2Mo_{10}O_{40}]$Aerogel-MgO | 2.5 | 49.7 | 47.8 |
| 3522 | $[Ag_5PV_2Mo_{10}O_{40}]$ZnO | 2.5 | 50.1 | 47.5 |
| 3524 | $[Ag_5PV_2Mo_{10}O_{40}]$Aerogel-$TiO_2$ | 2.6 | 49.8 | 47.6 |
| 3633 | [2 mol % $(Ce(NO_3)_3$ + $Cu(NO_3)_2)$]Aerogel-$TiO_2$ | 2.5 | 50 | 47.5 |

Abbreviations:
PTFE: poly(tetrafluoroethylene) available as F5A powder from Ausimont, Morristown, NJ
PFPE: perfluoropolyether available as FOMBLIM ™ Y25 oil from Ausimont, Morristown, NJ
Percentages are weight percents For purposes of description, there are 3 hierarchies, gradations, designations or classes of POMs. The first, most encompassing class of the 3 below covers all POMs of the Keggin class. The second gradation or class is those POMs that contain vanadium (V) centers as the redox active component, and the third class are the POMs listed in Table 1 above.

POMs—First Class:

$Y_n[XM_xM'_{12-x}O_{40}]$, where M=redox active d-block or f-block metal, including $d^0$ centers such as V(V), x=1–6, M'=Mo(VI) and/or W(VI), Y=the counter cations, which can be s-block metals (e.g. Na(I), Ca(II), etc.), d-block metals (e.g. Ag(I), Cu(II), Au(III), etc.), f-block metals (e.g. Ce(IV), etc.), or p-block based cations such as tetra-n-butylammonium, or any combination of these 4 classes of counter cations, and n=the number of counter cations, A, such that their combined positive charge equals the negative charge on the POM unit, $[XM_xM'_{12-x}O_{40}]^{n-}$.

POM Second Class:

The POMs above, but where M=V(V).

POM Third Class:

$H_5PV_2Mo_{10}O_{40}$, $Ag_5PV_2Mo_{10}O_{40}$, or $Na_5PV_2Mo_{10}O_{40}$.

The percent values assigned to the above listed components of the example skin protectant formulations are given for example only. These values may be adjusted up or down and still embody the spirit of the invention if the herein described qualities of efficacy and composition of the present invention are met. The active moiety may be present in the range of about 1–20%, the PFPE may be present in the range of about 40–60% and the PTFE may be present in the range of about 30–50%.

All active moieties listed above are useful for both liquid and vapor challenges. The active moieties are polyoxometalates or metal salts suspended on reactive nanoparticles. These POMs were suspended either on conventionally prepared nanoparticulate zinc oxide (ICD 3520) or on aerogel prepared nanoparticulate titanium dioxide or magnesium oxide (ICD 3522, 3524). The metal salts were suspended on aerogel prepared nanoparticulate titanium dioxide (ICD 3633). The process for the preparation of aerogel metal oxides is covered in a patent filed by Klabunde et al (U.S. Pat. No. 6,087,294) and Utarpanya et al., Chem Mater. 3:175–181 (1991), incorporated herein by reference. The amount of each varies with each formulation. The object is to optimize the quantity of active moiety in the base cream without loosing the barrier properties of the base cream. One criterion for selection of the active materials is increased efficacy against HD and/or GD vapor. Formulations that have significantly (P=0.05) increased protection compared to SERPACWA (ICD 3004) in the penetration cell model against HD and GD are listed in the results section. The best candidate compound listed in Table 1 for both HD and GD is ICD 3524 ($[Ag_5PV_2Mo_{10}O_{40}]TiO_2$).

The POM/RNP must also be incorporated into the TSP matrix without degradation of the barrier properties. These materials were incorporated into the cream either as solids or aqueous suspensions. Typically they are dispersed into the perfluorinated oil followed by sequential addition of the appropriate amount of F5A poly(tetrafluoroethylene).

SERPACWA (ICD 3004) consists of fine particles of poly(tetrafluoroethylene) resin dispersed in perfluorinated polyether oil. The excellent barrier properties of this high molecular weight polymer formulation are related to the low solubility of most materials in it. Only highly fluorinated solvents like Freon® have been observed to show appreciable solubility. This aprotic non-polar polymer mixture provides a unique medium for active moieties of the invention. Reaction mechanisms that do not involve charged transition states should be favored in this chemical environment.

Base creams formed from about 35–50% fine particulates of certain poly(tetrafluoroethylene) PTFE resins dispersed in perfluorinated polyether oils (PFPE) having viscosities from about 20 cSt to about 500 cSt afford good protection against chemical warfare agents such as HD, L, sulfur mustard/Lewisite mixtures (HL), pinacolyl methylphosphonofluoridate (soman or GD)), thickened soman (TGD) and O-ethyl S-(2-diisopropylaminoethyl)methylphosphonothiolate (VX). PTFE and PFPE are available commercially from Ausimont (Morristown, N.J.) and Dupont (Wilmington, Del.).

The base creams used in the invention are suspensions of 35–50% finely divided PTFE having a surface area below about 6 $m^2/g$ in a perfluorinated polyether base oil prepared from perfluoropropylene oxide, which has a viscosity between about 20 and about 500 cSt. More preferred compositions comprise from about 35% to about 50% of finely divided PTFE having an average particle size from about 0.1 $\mu m$ to about 10 $\mu m$ and a surface area below about 4 $m^2/g$ in a perfluorinated polyether base oil from 40% to 60% having a viscosity between about 20 and about 500 cSt.

Suitable perfluorinated polyether oils are Fomblin® HC- and Y-oils (Ausimont) and Krytox® oils (Dupont). The Fomblin® oils are mixtures of linear polymers based on perfluoropropylene oxide having the following chain structure: $CF_3-[(OCF(CF_3)CF_2)_n-(OCF_2)_m]OCF_3$. The Krytox® oils are mixtures of linear polymers also based on perfluoropropylene oxide and have the chemical structure $F-[(CF(CF_3)CF_2O)]_mCF_2CF_3$. Fomblin® Z oils having the formula: $CF_3-[(OCF_2CF_2)_n-(OCF_2)_m]-OCF_3$, may also be useful in the practice of the invention. The indices n and m indicate the average number of repeating polymeric subunits in the oil molecules. The oils may have a viscosity of about 20 cSt to about 500 cSt or more. The creams were generally prepared according to U.S. Pat. No. 5,607,979, incorporated herein in its entirety.

Other additives to the base cream are water and surfactant and other chemical necessary to maintain activity (see Table 1). The surfactant facilitates the mixing of the water with the base cream. An example of a typical surfactant is perfluoropolyalkylether (Krytox® CAS # 60164-51-4 from Dupont). Additional materials may also be incorporated as long as they do not reduce effectiveness of the topical protectant, such as stabilizers, camouflage paints, and sunscreens.

A further understanding of the composition of the topical protectant of the invention can be obtained by reference to certain specific example formulations set forth in Table 1. These examples are provided herein for purposes of illustration only and are not intended to be limiting. Many active moieties require the presence of water as a reagent for the hydrolysis of HD and GD. The active moieties that react by a hydrolysis mechanism require the presence of water. When the topical protectant is applied to the skin of a user, moisture in the form of perspiration may also aid in the hydrolysis of HD and GD. The addition of perfluorinated polyether surfactants to the base cream facilitates the addition of water.

Description of Mixing the POMs and RNPs

Supporting polyoxometalates or metal salts on the reactive nanoparticles is a relatively straightforward procedure. Depending on the oxygen sensitivity of the material, some of the polyoxometalate/metal salt/reactive nanoparticle materials may be held under inert atmosphere during the procedure. The procedure may be generally described by dissolving the desired amount of polyoxometalate or metal salt in an appropriate solvent and then adding the desired amount of reactive nanoparticle material to the solution. Mechanical mixing times of 10–20 minutes are usually sufficient for the adsorption of the polyoxometalate or metal salt onto the surface of the reactive nanoparticle. A typical procedure for the preparation of polyoxometalate or metal salt supported on reactive nanoparticles is presented below.

In a 50 ml septum capped round bottom flask is placed 30 ml of toluene or other suitable solvent. Added to this is 0.4582 g of $Na_5PV_2Mo_{10}O_{40}$. The solution is stirred to dissolve the polyoxometalate and then 0.5000 g of Aerogel prepared nanoparticulate MgO is added. The polyoxometalate/reactive nanoparticle mixture is allowed to stir overnight. After stirring, the solvent and polyoxometalate/reactive nanoparticle formulation are separated either through filtration or vacuum evaporation of the solvent. This yields approximately 0.95 grams of 2 mol % $Na_5PV_2Mo_{10}O_{40}$ polyoxometalate supported on Aerogel prepared nanoparticulate MgO.

Temperature and mixing sheer should be monitored to maintain the base cream at the desired consistency and quality. The active TSPs are typically prepared at ambient temperature using mechanical mixing. Depending on the oxygen sensitivity of the active material, some of the polyoxometalate/metal salt/reactive nanoparticle formulation may be added to the perfluorinated oil under an inert (i.e. nitrogen) atmosphere. Mixing times of 10–20 minutes are usually sufficient for dispersal of the polyoxometalate/metal salt/reactive nanoparticle formulation into the SERPACWA matrix. A typical procedure for the preparation of an active aTSP with a POM/metal salt/reactive nanoparticle formulation is presented below:

In a polypropylene container is added the appropriate amount of POM/RNP (1–3% by weight) and Y25 (50–55% by weight) perfluorinated oil. The suspension is mixed with a mechanical stirrer at ambient temperature for 5 to 15 minutes. To the suspension is added F5A poly (tetrafluoroethylene) in three portions with vigorous mechanical stirring for 5 to 10 minutes between each addition. After final addition the container is tightly capped and sealed with Parafilm®.

Multilayer Approach

Although an active TSP can be generally the application of a powder that is a POM/RNP sprinkled on the skin, or an active moiety in a base cream wherein the cream is spread on the skin, a multilayering approach can also be used. The multilayer approach would be to use the active TSP as the first layer and a solid active moiety powder as the second layer. The second layer would be a thin coating of the solid active moiety powder sprinkled over the active TSP cream. This approach would provide a concentrated decontamination material at the surface of the barrier cream, which would accelerate the neutralization process of CWA's coming in contact with the surface. In the alternative, the solid active moiety powder can be applied first followed by an application of the active TSP.

Testing

Evaluation of formulations was conducted with a decision tree network (DTN) that describes the path that active TSPs follow during evaluation (FIG. 1).

The DTN is divided into two pathways: one for vesicants and the other for nerve agents. Within these pathways there are three blocks each with a decision point. The first block consists of a series of three mechanical (in vitro) modules used to determine the initial efficacy of candidate formulations and to eliminate non-effective candidates before animal testing, the second block consists of in vivo modules and the third block consists of an advanced animal module to determine the influence of time, water and interactions with other products.

The M8 paper test is used to evaluate the barrier resistance of liquid CWA challenges, including HD, pinacolyl methylphosphonofluoridate (soman, GD), and O-ethyl S-(2-diisopropylaminoethyl) methylphosphonothioate (VX). In this test a 0.15 mm layer of active TSP is placed over a well-defined area of M8 chemical detection paper and challenged with an 8 $\mu$l droplet of CWA. When agent penetrates the active TSP barrier and reaches the M8 paper, a colored spot develops on the paper. The test assemblies are observed for 6 hr and the breakthrough time is reported for each sample. A total of nine replicates are run for each test, and a standard reference compound is included each day for quality control.

The penetration cell test is used to evaluate the barrier properties against both liquid and vapor CWA challenges (Braue, E. H. Jr. *Journal of Applied Toxicology*, 1999, 19(S), S47–S53). In this test the lower half of a Reifenrath diffusion cell (Reifenrath Consulting and Research, Richmond, Calif.) is used. A 0.15 mm thick layer of active TSP is supported by nitrocellulose paper on top of the cell. The active TSP layer is challenged with a 10-ul liquid droplet of HD or an 8 $\mu$l droplet of GD, or a saturated vapor cup of HD or GD. Breakthrough of CWA into the lower chamber of the diffusion cell is monitored using a miniature continuous air monitoring system (MINICAMS, CMS Research, Birmingham, Ala.). This system has been automated to allow continuous monitoring of five cells in a 40-min cycle. The test runs for 20 hr and the accumulated amounts of agent that break through the active TSP barrier are calculated. From these data, we obtained two values: the cumulative amount of CWA that penetrates through the active TSP, and the time at which a "breakthrough" occurs. We defined "breakthrough" values at the minimum amount of HD (1000 ng) and GD (1000 ng) that results in a physiological response. Minimal amount of HD for vesication=1000 ng. See F. R. Sidell, J. S. Urbanetti, W. J. Smith, and C. G. Hurst in *Textbook of Military Medicine, Medical Aspects of Chemical and Biological Warfare*, edited by F. R. Sidell, E. T. Takafuji, and D. R. Franz (Office of the Surgeon General at TMM Publications, Washington, D.C. 1997) p 201. $LD_{50}$ for soman (GD)=350 mg(70 kg man. See F. R. Sidell in *Textbook of Military Medicine, Medical Aspects of Chemical and Biological Warfare*, edited by F. R. Sidell, E. T. Takafuji, and D. R. Franz (Office of the Surgeon General at TMM Publications, Washington, D.C. 1997) p 141. These two values allow us to rank the active TSP formulations and to select the appropriate component for advanced development.

The proof-of-neutralization test is used to verify that active TSP formulations actually neutralize CWAs into less toxic materials. This test uses the headspace solid phase microextraction (HS-SPME) technique for the collection of CWAs. Samples collected on the extraction filament are analyzed by gas chromatography/mass spectroscopy. 100 mg of active TSP formulation are challenged with 0.11 $\mu$l of neat CWA (HD, GD, or VX) in a small vial. The headspace above the mixture is sampled periodically to determine the amount of CWA remaining in the flask. Efficacy is determined by the % loss of CWA. Other analytical techniques such as Nuclear Magnetic Resonance (NMR) and Fourier-Transform Infrared Spectrometry (FTIR) have also been used in this module.

Formulations that pass this initial set of screens are moved into the second phase of testing using animal models. The weanling pig test for HD vapor evaluates a 0.10 to 0.20 mm thick layer of active TSP spread on the depilated dorsa. The standard saturated vapor cup is used for a 15–60 min challenge. The effectiveness of the active TSP is determined by measuring the degree of erythema that developed on the skin exposure site. Erythema is measured objectively using a reflectance calorimeter (see Braue, E. H. Jr. *Journal of Applied Toxicology*, 1999, 19(S), S47–S53).

The rabbit lesion area ratio (LAR) test is used to evaluate a challenge by HD liquid. In this test, a 0.10 mm layer of active TSP spread on the clipped dorsa is challenged with 1.0 $\mu$l of liquid HD. The effectiveness of the active TSP is determined by measuring the lesion areas of protected and non-protected sites.

The rabbit acetyl cholinesterase (AChE) inhibition test is performed by applying a 0.10 mm thick layer of active TSP on the clipped dorsa of rabbit followed by a fixed dose of GD (1 $LD_{50}$), TGD (1 $LD_{50}$), or VX (20 $LD_{50}$). The effectiveness of the active TSP is determined by lethality and also by measuring the erythrocyte acetyl cholinesterase activity 0.5, 1, 2, and 24 hr following exposure.

Candidate formulations that pass the in vivo test modules move into advanced animal testing. These tests are similar to the initial animal tests with the addition of stresses for wear-time and washing with water. Interactions with other products that a soldier might use are also evaluated. These products include camouflage paints, sunscreens and insecticides.

Results

The polyoxometallate/metal salt/reactive nanoparticle composite will react to neutralize sulfur mustard via oxidation and/or dehydrohalogenation (Scheme 1)

Scheme 1
Possible neutralization reactions of [POM]RNP with HD

These oxidations of dialkylsulfides have been reported for POMs (Gall, R. D., Hill, C. L.; Walker, J. E. *Chem. Mater.* 1996, 8, 2523). Also, the reactions of HD with reactive nanoparticles (Wagner, G. W.; Koper, O. B.; Lukas, E.; Decker, S.; Klabunde, K. J. *J. Phys. Chem. B.* 2000, 104, 5118) has been reported.

Against GD vapor, the most effective moiety was the ICD 3524 ($[Ag_5PV_2Mo_{10}O_{40}]TiO_2$) that reduced the amount of GD by 59% compared to TSP alone. In this case, it is likely that the $TiO_2$ is acting as the active species (Scheme 2).

Scheme 2
Hydrolyses of soman (GD) with [POM]TiO$_2$ active TSP

The GD may also be physically adsorbed by the POM/RNP or it is possible that adventitious adsorbed water in the POM/RNP complex may act as a reagent for hydrolysis presented above.

In the first mechanical test, the M8 paper, POM/RNP formulations were tested against HD (ICD #3520, 3522, and 3524), GD (ICD #3522, and 3524), and VX liquid (ICD #3520, 3522, and 3524) (Chart 1).

CHART 1

Breakthrough time and % breakthrough for [POM]RNP containing active TSPs.

M8 Data

Legend:
- HD time
- GD time
- VX time
- ▲ HD % break
- × GD % break
- + VX % break Chart 1. Breakthrough time and % breakthrough for [POM]RNP containing active TSPs.

CHART 2

Time for 1000 ng GD to penetrate aTSPs with POM/RNP active TSPs.

GD vapor penetration cell data time to 1000 ng

All POM/RNP containing active TSPs displayed equivalent or better barrier against liquid challenges as compared to SERPACWA (ICD 3004). Furthermore, ICD 3520 ([$Ag_5PV_2Mo_{10}O_{40}$]Aerogel-MgO) displayed no breakthroughs over 360 minutes for both HD and VX liquid. From the above chart it appears that ICD 3524 has the best barrier properties against liquid challenges. The increase in protection for the POM/RNP active TSPs was impressive against GD vapor as seen by the increase in the time for 1000 ng of GD vapor to penetrate the active TSP as compared to SERPACWA (ICD 3004) (Chart 2).

Chart 2. Time for 1000 ng GD to penetrate aTSPs with POM/RNP active TSPs.

A comparison of the cumulative amount of GD vapor that penetrates the active TSP over 20 hours also demonstrates the efficacy or POM/RNP active TSPs (Chart 3).

CHART 3

Cumulative amount of GD vapor through aTSP over 20 hr.

Chart 3. Cumulative amount of GD vapor through aTSP over 20 hr.

Formulation ICD 3524 shows the greatest protection against GD vapor reducing the amount of GD by 59%. Due to high variability in the results, only ICD 3524 shows significantly (P=0.05) increased protection compared to SERPACWA (ICD 3004) in the penetration cell model against GD.

The increase in protection for the RNP/POM was also remarkable against HD vapor as demonstrated in the increase in the time needed for 1000 ng of HD vapor to penetrate the active TSP as compared to SERPACWA (ICD 3004) (Chart 4).

CHART 4

Time for 1000 ng HD to penetrate active TSPs containing RNP/POM.

Chart 4. Time for 1000 ng HD to penetrate active TSPs containing RNP/POM.

A comparison of the cumulative amount of HD vapor that penetrates the active TSP over 20 hours also shows the increase in protection (Chart 5).

CHART 5

Cumulative amount of HD vapor through aTSP over 20 hr.

Chart 5. Cumulative amount of HD vapor through aTSP over 20 hr.

As clearly seen in Chart 5, only ICD 3520 ($[Ag_5PV_2Mo_{10}O_{40}]MgO$) and ICD 3524 ($[Ag_5PV_2Mo_{10}O_{40}]TiO_2$) show significant efficacy (P=0.05) against HD vapor compared to 3004 (ICD 3004) in the penetration cell model. In fact, as few as 54 ng of HD vapor penetrate the aTSP barrier in 20 hr.

Despite the excellent performance of the active TSPs containing polyoxometalate in the penetration cell models, the results from the weanling pig model were more varied (Chart 6).

CHART 6

Results of active TSPs containing POM/RNP complexes.

Chart 6. Results of active TSPs containing POM/RNP complexes.

The active TSPs containing POM/RNP complexes reduced the cumulative amount of HD vapor in the penetration cell by up to 90% (Chart 4). The recorded erythema from HD vapor in these active TSPs, however, is not significantly decreased above control in the in vivo test. We offer four possible explanations. First, the skin is occluded by the aTSP, increasing agent penetration and thus the observed erythema. Second, the skin may be sensitized by the aTSP, and thus the small amount of HD vapor that penetrates the skin results in greater erythema. Third, the skin may be irritated by the reaction products. And fourth, agent may penetrate the aTSP during exposure and not be completely removed by the cleaning procedure.

Having now fully described the invention, it will be apparent to one of ordinary skill in the art that many changes and modifications can be made thereto without departing from the spirit or scope of the invention as set forth herein.

What is claimed is:

1. A topical skin protectant formulation for neutralizing chemical warfare agents into less toxic products comprising: a barrier base cream; and one or more polyoxometalate suspended on reactive nanoparticles or metal salt suspended on reactive nanoparticles as an active moiety.

2. The topical skin protectant formulation of claim 1, wherein the base cream comprises poly(tetrafluoroethylene) resins dispersed in perfluorinated polyether oils.

3. The topical skin protectant formulation of claim 1, wherein said polyoxometalate or metal salt comprises $Na_5PV_2Mo_{10}O_{40}$, $Ag_5PV_2Mo_{10}O_{40}$, $H_5PV_2Mo_{10}O_{40}$, $Ce(NO_3)_3$, or $Cu(NO_3)_2$, and said reactive nanoparticle is conventionally prepared nanoparticulate MgO, ZnO, CaO, $TiO_2$ or $CeO_2$; or Aerogel prepared nanoparticulate MgO, ZnO, CaO, $TiO_2$, or $CeO_2$.

4. A topical skin protectant formulation for neutralizing chemical warfare agents into less toxic products comprising:
(a) a barrier base cream, said barrier base cream comprising poly(tetrafluoroethylene) resins dispersed in perfluorinated polyether oils; and
(b) one or more active moieties complex comprising a polyoxometalate or metal salt suspended on reactive nanoparticles, wherein said polyoxometalate or metal salt comprises: $Na_5PV_2Mo_{10}O_{40}$, $Ag_5PV_2Mo_{10}O_{40}$, $H_5PV_2Mo_{10}O_{40}$, $Ce(NO_3)_3$, or $Cu(NO_3)_2$, and said reactive nanoparticle is one or more conventionally prepared nanoparticulate MgO, ZnO, CaO, $TiO_2$ or $CeO_2$; or Aerogel prepared nanoparticulate MgO, ZnO, CaO, $TiO_2$, or $CeO_2$.

5. The topical skin protectant formulation of claim 4, further comprising one or more additives.

6. The topical skin protectant formulation of claim 5, wherein said additives comprise one or more of water, stabilizers, surfactants, camouflage paints, and sunscreens.

7. A topical skin protectant formulation for neutralizing chemical warfare agents into less toxic products comprising:
(a) a barrier base cream, said barrier base cream comprising poly(tetrafluoroethylene) resins dispersed in perfluorinated polyether oils;
(b) one or more active moiety complex comprising a polyoxometalate or metal salt suspended on reactive nanoparticles, wherein said polyoxometalate or metal salt comprises: $Na_5PV_2Mo_{10}O_{40}$, $Ag_5PV_2Mo_{10}O_{40}$, $H_5PV_2Mo_{10}O_{40}$, $Ce(NO_3)_3$, or $Cu(NO_3)_2$ and said reactive nanoparticle is one or more conventionally prepared nanoparticulate MgO, ZnO, CaO, $TiO_2$ or $CeO_2$; or Aerogel prepared nanoparticulate MgO, ZnO, CaO, $TiO_2$, or $CeO_2$; and
(c) one or more additives.

8. The topical skin protectant formulation of claim 7, wherein said additives comprise one or more of water, surfactants, stabilizers, camouflage paints, and sunscreens.

9. A topical skin protectant system comprising:
(a) a topical skin protectant formulation for neutralizing chemical warfare agents into less toxic products comprising a barrier cream and one or more active moieties, said active moieties comprising polyoxometalates and/or metal salts and/or reactive nanoparticles; and
(b) a second formulation for applying a thin solid active moiety powder on top or below said topical skin protectant formulation comprising one or more polyoxometalates and/or metal salts and/or reactive nanoparticles.

10. The topical skin protectant system of claim 9, wherein said one or more active moieties in the topical skin protectant formulation and in the solid active moiety powders are one or more active moieties comprising a complex comprising one or more conventionally prepared nanoparticulate MgO, ZnO, CaO, $TiO_2$ or $CeO_2$; or Aerogel prepared nanoparticulate MgO, ZnO, CaO, $TiO_2$, or $CeO_2$ and a polyoxometalate or metal salt comprising $Na_5PV_2Mo_{10}O_{40}$, $Ag_5PV_2Mo_{10}O_{40}$, $H_5PV_2Mo_{10}O_{40}$, $Ce(NO_3)_3$, or $Cu(NO_3)_2$.

11. A method of protecting a user against chemical warfare agents comprising: applying a topical skin protectant formulation for neutralizing chemical warfare agents into less toxic products comprising:
(a) a barrier cream; and
(b) one or more active moieties, said one or more active moieties comprising polyoxometalates and/or metal salts and/or reactive nanoparticles.

12. A method of protecting a user against chemical warfare agents comprising:
(a) applying a first thin layer of solid active moiety powder comprising one or more polyoxometalates and/or metal salts and/or reactive nanoparticles; and
(b) applying a second layer of a topical skin protectant formulation for neutralizing chemical warfare agents into less toxic products comprising a barrier cream and one or more active moieties comprising one or more complex of one or more polyoxometalates and/or one or more metal salts and/or reactive nanoparticles.

13. The method of claim 12, wherein said one or more active moieties in the topical skin protectant formulation and in the solid active moiety powder are polyoxometalates and/or metal salts and/or reactive nanoparticles selected from the group consisting of:
(a) $[Na_5PV_2Mo_{10}O_{40}]TiO_2$,
(b) $[Ag_5PV_2Mo_{10}O_{40}]$Aerogel-MgO,
(c) $[Ag_5PV_2Mo_{10}O_{40}]ZnO$,
(d) $[Ag_5PV_2Mo_{10}O_{40}]$Aerogel-$TiO_2$, and
(e) $[2\ mol\ \%\ (Ce(NO_3)_3+Cu(NO_3)_2)]$Aerogel-$TiO_2$.

14. A method of protecting a user against chemical warfare agents comprising:
(a) applying a first layer of a topical skin protectant formulation for neutralizing chemical warfare agents into less toxic products comprising a barrier cream and one or more active moieties, said one or more active moieties comprising one or more polyoxometalates and/or metal salts and/or reactive nanoparticles; and
(b) applying a thin layer of solid active moiety powder over the first layer, said solid active moiety powder comprising one or more polyoxometalates and/or metal salts and/or reactive nanoparticles.

15. The method of claim 14, wherein said one or more active moieties in the topical skin protectant formulation and in the solid active moiety powder are polyoxometalates and/or metal salts and/or reactive nanoparticles selected from the group consisting of:
(a) $[Na_5PV_2Mo_{10}O_{40}]TiO_2$,
(b) $[Ag_5PV_2Mo_{10}O_{40}]$Aerogel-MgO,
(c) $[Ag_5PV_2Mo_{10}O_{40}]ZnO$,
(d) $[Ag_5PV_2Mo_{10}O_{40}]$Aerogel-$TiO_2$, and
(e) $[2\ mol\ \%\ (Ce(NO_3)_3+Cu(NO_3)_2)]$Aerogel-$TiO_2$.

16. A method of making a topical skin protectant formulation comprising: mixing:
a) one or more active moieties comprising polyoxometalates and/or metal salts and/or reactive nanoparticles: with
b) a barrier cream comprising poly(tetrafluoroethylene) resins dispersed in perfluorinated polyether oils.

17. The method of claim 16, wherein said polyoxometalates and/or metal salts and/or reactive nanoparticles are selected from the group consisting:

(a) $[Na_5PV_2Mo_{10}O_{40}]TiO_2(N)$, (b) $[Ag_5PV_2Mo_{10}O_{40}]$Aerogel-MgO, (c) $[Ag_5PV_2Mo_{10}O_{40}]$ZnO, (d) $[Ag_5PV_2Mo_{10}O_{40}]$Aerogel-TiO$_2$, and (e) $[2 \text{ mol }\% (Ce(NO_3)_3+Cu(NO_3)_2)]$Aerogel-TiO$_2$.

18. A topical skin protectant formulation comprising a formulation selected from the group consisting of:

(a) about 5 wt. % of polyoxometalate $Na_5PV_2Mo_{10}O_{40}$ on titanium dioxide, about 48 wt. % perfluoropolyether oil, about 48 wt. % perfluoropolyethylene;

(b) about 4 wt. % of polyoxometalate $Ag_5PV_2Mo_{10}O_{40}$ on aerogel prepared magnesium oxide about 50 wt. % perfluoropolyether oil, about 48 wt. % perfluoropolyethylene;

(c) about 3 wt. % polyoxometalate $Ag_5PV_2Mo_{10}O_{40}$ on zinc oxide, about 50 wt. % perfluoropolyether oil, about 48 wt. % perfluoropolyethylene;

(d) about 3 wt. % polyoxometalate $Ag_5PV_2Mo_{10}O_{40}$ on aerogel prepared titanium dioxide, about 50 wt. % perfluoropolyether oil, about 48 wt. % perfluoropolyethylene; and (e) about 2.5 wt. % metal salt $Ce(NO_3)_3$ and $Cu(NO_3)_2$ on titanium dioxide, about 50 wt. % perfluoropolyether oil, about 47.5 wt. % perfluoropolyethylene.

19. A topical skin protectant formulation for neutralizing chemical warfare agents into less toxic products comprising:

(a) a barrier base cream, said barrier base cream comprising about 30–50 wt. % poly(tetrafluoroethylene) resins dispersed in about 40–60 wt. % perfluorinated polyether oils; and (b) about 1–20 wt. % active moiety, said active moiety comprising a complex of a polyoxometalate and/or metal salt suspended on reactive nanoparticles; said reactive nanoparticles selected from the group consisting of one or more conventionally prepared nanoparticulate MgO, ZnO, CaO, TiO$_2$ or CeO$_2$; or Aerogel prepared nanoparticulate MgO, ZnO, CaO, TiO$_2$, or CeO$_2$ and said one or more polyoxometalates or metal salts selected from the group consisting of $Na_5PV_2Mo_{10}O_{40}$, $Ag_5PV_2Mo_{10}O_{40}$, and $H_5PV_2Mo_{10}O_{40}$, $Ce(NO_3)_3$, or $Cu(NO_3)_2$.

20. A topical skin protectant formulation for neutralizing chemical warfare agents into less toxic products comprising: an active moiety, wherein said active moiety is a polyoxometalate of the formula $Y_n[XM_xM'_{12-x}O_{40}]$, where M=redox active d-block or f-block metal, including $d^0$ centers such as V(V), x=1–6, M'=Mo(VI) and/or W(VI), Y=the counter cations, which can be s-block metals (e.g. Na(I), Ca(II), etc.), d-block metals (e.g. Ag(I), Cu(II), Au(III), etc.), f-block metals (e.g. Ce(IV), etc.), or p-block based cations such as tetra-n-butylammonium, or any combination of these four classes of counter cations, and n=the number of counter cations, A, such that their combined positive charge equals the negative charge on the POM unit, $[XM_xM'_{12-x}O_{40}]^{n-}$.

21. The topical skin protectant of claim 20, further comprising a base cream.

22. A topical skin protectant formulation for neutralizing chemical warfare agents into less toxic products comprising one or more active moieties, wherein said one or more active moiety is a complex comprising a polyoxometalate or metal salt suspended on reactive nanoparticles.

23. The topical skin protectant formulation of claim 1, wherein said chemical warfare agents are one or more of the group consisting of blistering agents, G class nerve agents, and VX.

24. The topical skin protectant formulation of claim 23, wherein said blistering agent is sulfur mustard.

25. The topical skin protectant formulation of claim 23, wherein said G class nerve agent is soman.

* * * * *